United States Patent [19]

Apotheker, deceased

[11] E Re. 31,324

[45] Reissued Jul. 26, 1983

[54] FLUORINE CONTAINING ORGANOSILICON COMPOUNDS

[75] Inventor: David Apotheker, deceased, late of Wilmington, Del., by Bank of Delaware, executor

[73] Assignee: E. I. Du Pont de Nemours and Company, Wilmington, Del.

[21] Appl. No.: 367,756

[22] Filed: Apr. 12, 1982

Related U.S. Patent Documents

Reissue of:

[64] Patent No.: 4,308,393
Issued: Dec. 29, 1981
Appl. No.: 195,094
Filed: Oct. 8, 1980

[51] Int. Cl.[3] ..... C07F 7/08; C07F 7/18

[52] U.S. Cl. ..... 556/445; 556/448; 556/450; 556/459; 556/460

[58] Field of Search ..... 556/448, 450, 460, 459, 556/445

[56] References Cited

U.S. PATENT DOCUMENTS

| | | | |
|---|---|---|---|
| 2,958,707 | 11/1960 | Warrick | 556/450 |
| 3,132,117 | 5/1964 | Schmidt | 556/448 X |
| 3,148,201 | 9/1964 | Fassnacht | 556/450 X |
| 3,322,721 | 5/1967 | Howard | 260/46.5 |
| 3,331,813 | 7/1967 | Pittman et al. | 556/448 X |
| 3,334,123 | 8/1967 | Culpepper | 556/448 |
| 3,422,131 | 1/1969 | Pittman et al. | 556/448 |
| 3,529,003 | 9/1970 | Rausch et al. | 556/448 |
| 3,716,518 | 2/1973 | Pittman et al. | 556/445 X |
| 3,859,320 | 1/1975 | Atherton | 556/445 X |
| 3,876,677 | 4/1975 | Wu | 556/448 |
| 4,031,119 | 6/1977 | Ponomarev et al. | 556/448 |
| 4,085,137 | 4/1978 | Mitsch | 557/445 X |
| 4,089,882 | 5/1978 | Takamizawa et al. | 556/460 X |

FOREIGN PATENT DOCUMENTS 1023717 3/1966 United Kingdom .

*Primary Examiner*—Paul F. Shaver

[57] ABSTRACT

Addition to organosilicon compounds having at least one alkyl group attached to a silicon atom, at least one hydrogen atom being attached to the carbon atom adjacent the silicon atom, of a fluorocompound, which may be a fluoroolefin [, a perfluoroketone,] or a perfluoroether having a carbon-carbon double bond in α-position to the ether oxygen atom, give fluorine-containing organosilicon compounds. These adducts may be liquid or solid and are useful as (1) lubricants and sealants for automotive and aerospace industries (2) fire-resistant hydraulic fluids, and (3) siloxane elastomers having good oil and lubricant resistance.

4 Claims, No Drawings

FLUORINE CONTAINING ORGANOSILICON COMPOUNDS

Matter enclosed in heavy brackets [ ] appears in the original patent but forms no part of this reissue specification; matter printed in italics indicates the additions made by reissue.

BACKGROUND OF THE INVENTION

This invention relates to fluorine-containing organosilicon compounds which are made by the addition of certain unsaturated fluorocarbons and ethers or saturated fluoroketones to organosilicon compounds having a hydrogen atom bonded to a carbon atom bonded to a silicon atom.

It is known to add unsaturated organic compounds including certain unsaturated fluorocarbons to organosilicon compounds. The basic disclosure in this field is U.S. Pat. No. 2,958,707 to Warrick. A single fluorinated unsaturated compound, chlorotrifluoroethylene, failed, however, to give a single or even predominant well-defined addition product with various organosilicon compounds. Many solid and liquid fractions were obtained and could not be well identified, except that some of their physical properties were determined.

U.S. Pat. No. 3,148,201 to Fassnacht comments on the Warrick process that is conductive to telomerization and polymerization, so that a variety of reaction products are obtained. Fassnacht proposes a different process, starting with a polyfluoroalkyl-substituted cyclic polysiloxane, so that a well-defined product having a predictable sequence of repeating units is made.

The fluoroalkyl-substituted organosilicon compounds of Warrick and Fassnacht are said to have many applications, including use as lubricants, especially where high loads are present. However, neither one of these two patents provides a technique for making nonpolymeric addition products. Yet, such simple adducts would be very desirable because of better product design and quality control.

SUMMARY OF THE INVENTION

According to this invention, there is now provided a class of fluorine-containing organosilicon compounds which are made by the addition to organosilicon compounds having at least one alkyl group attached to a silicon atom, at least one hydrogen atom being bonded to the carbon atom adjacent the silicon atom, of a fluorocompound selected from the class consisting of the following:

(A) fluoroolefins having one of the following formulas (1), (2), and (3):

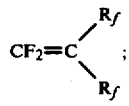

(1)

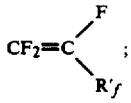

(2)

-continued

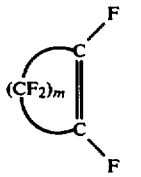

(3)

[(B) ketones having the following formula (4):]

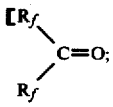

(4)

and (C) ethers having the following formula [(5)] *(4)*

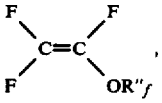

[(5)] *(4)* where each $R_f$ independently is a $C_1$–$C_8$ saturated perfluoroalkyl;

$R'_f$ is Br or $R_f$;

$R''_f$ is $R_f$ or a radical obtained by removing one fluorine atom from a perfluoroalkyl ether; and m in formula (3) is an integer of 2 to 12.

DETAILED DESCRIPTION OF THE INVENTION

With a minor modification, the organosilicon compounds suitable as the starting materials in the process of this invention are those described in the Warrick patent, U.S. Pat. No. 2,958,707. These may be monomeric, oligomeric, or polymeric organosilicon compounds having at least one $C_1$–$C_4$ alkyl radical per molecule and being substantially free of Si—H bonds and of groups having ethylenic unsaturation. The term "substantially free" means that trace amounts of compounds having Si—H bonds or ethylenic unsaturation, often present in commercial organosilicon compounds, may be present.

The remaining valences of the silicon atom may be satisfied with any other known type of group. For example, suitable organosilicon compounds may have one of the following formulas (6), (7), and (8), which represent either a monomeric compound or a repeating unit of an oligomeric or polymeric compound:

$$R_aR'_bSiX_cO_{\frac{4-a-b-c}{2}} \quad (6)$$

$$R_aR_bSiX_cR''_{\frac{4-a-b-c}{2}} \text{ and} \quad (7)$$

$$R_xR'_yX_zSi-, \quad (8)$$

wherein a is an integer of 1–4; each of b and c is an integer of 0–3; x is an integer of 0–2; and each of y and z is an integer of 0–2; R is a $C_1$–$C_4$ alkyl; R' is an organic radical which bonds to the silicon atom through a carbon atom; with the proviso that at least one of R and R' is an alkyl which has a hydrogen atom bonded to the carbon atom bonded to the silicon atom; R″ is a saturated divalent hydrocarbon radical; and X is a hydrolyzable or condensable group; further provided that the silicon atom in formula (7) is bonded to another silicon atom.

R groups include methyl, ethyl, propyl and isopropyl, and the various isomers of the butyl group.

R′ typically will be an alkyl having 5 or more carbon atoms, for example, hexyl, dodecyl, and octadecyl; a cycloalkyl, for example, cyclopentyl or cyclohexyl; an aryl, such as phenyl, tolyl, or xylyl; a halohydrocarbon radical such as chloropentyl, chlorocyclohexyl, chlorooctadecyl, pentafluoroethyl, heptafluoropropyl, chlorophenyl, bromophenyl, and trifluorotolyl; or an organic radical having a functional group such, for example, as hydroxy, amino, carboxy, ether, ester, aldehyde, ketone, nitrile, nitro, amide, thiol, etc.; R″ is, for example, methylene, ethylene, propylene, phenylene, xylylene, or cyclohexylene; and X can be, among others, hydroxyl, amino, sulfide, halogen, or OR‴ group, wherein R‴ is a monovalent hydrocarbon radical free of ethylenic unsaturation, such as, methyl, hexyl, octadecyl, cyclohexyl, phenyl, tolyl, benzyl, or naphthyl.

The organosilicon compounds suitable in the practice of the present invention thus can be of several types, including hydrolyzable silanes such as dimethyldichlorosilane, ethyltriisopropoxysilane, phenylmethyldiphenoxysilane, and butyltrichlorosilane; nonhydrolyzable silanes such as tetramethylsilane, dimethyldiphenylsilane, and ethylphenyldicyclohexylsilane; partially hydrolyzed silanes still containing hydrolyzable groups; silazanes such as dimethylsilazane, phenylmethylsilazane, and dimethyltetramethyldisilazane; organosilicon sulfides; silcarbanes; polysilanes; silanols; salts of silanes; and both completely condensed and partially condensed polysiloxanes.

The preferred organosilicon compounds are linear and cyclic siloxanes having the general formula (9), below:

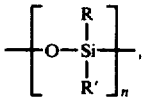

(9)

wherein each of R and R′ is alkyl, as earlier discussed in connection with the general formula (6); n is 3–6 for the cyclic silioxanes and 2–10,000 for linear siloxanes. An especially preferred class of organosilicon compounds represented by formula (9) are polydimethylsiloxanes. The terminal groups in the linear siloxanes of this type are hydroxyl groups, so that a hydrogen atom is attached to the free bond shown on the left hand side of formula (9), while a hydroxyl group is attached to the free bond on the right hand side.

The fluorocompound reactants can belong to any one of the [three] classes represented by the above formulas (1) through [(5).] (4). Typical fluoroolefins of formula (1) include, among others, octafluoroisobutylene, perfluoro-2-methylbutene, and perfluoro-2-ethylbutene. Those of formula (2) include hexafluoropropylene, bromotrifluoroethylene and perfluoro-1-butene. Typical cyclic fluoroolefins (3) are perfluorocyclobutene and perfluorocyclopentene.

[Representative perfluoroketones of formula (4) are: hexafluoroacetone, bis(perfluoroisopropyl) ketone, and perfluorocyclopentanone.]

Finally, typical perfluorovinyl ethers of formula [(5)] (4) can be, for example, simple compounds such as

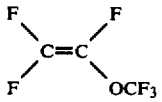

(10)

and

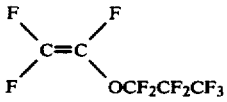

(11)

or telomerized or polymerized compounds such as

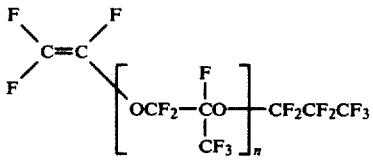

(12)

The fluorinated reactants selected for the process of this invention form with the organosilicon reactants simple addition products free of telomeric, oligomeric, or polymeric fragments, and uncontaminated by fluorinated homopolymers. Thus, fluoroolefins of formula (1) give products in which one or more hydrogen atoms bonded to carbon atoms adjacent the silicon atoms of the starting organosilicon compounds are replaced by the group

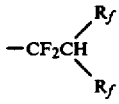

(13)

The fluoroolefins of formula (2) give products in which corresponding hydrogen atoms are replaced by the group

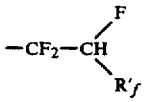

(14)

The cyclic fluorolefins of formula (3) introduce into the organosilicon compounds one or more groups

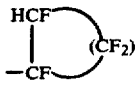

(15)

[The products obtained from the fluoroolefin (4) contain one or more groups]

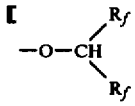

(16)

Finally, the products obtained from the fluoroethers [(5)] (4) will contain one or more groups

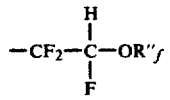

(17)

In all those products the indicated group replaces a hydrogen bonded to a carbon adjacent a silicon atom.

The products of the present invention are made by heating the reactants under autogeneous pressure in the presence of a free radical generator at about 100°-180° C. The reaction is considered complete when the pressure, which first builds up on heating but then decreases as the fluorinated reactant is being consumed, no longer changes. The product is isolated by an appropriate technique, such as, for example, removal of excess fluorinated reactant or fractional distillation.

The amount of the fluorinated reactant which adds to the organosilicon compound depends to a large extent on the relative proportions of the reactants. If the amount of the fluorinated compound is in a small excess over that required to react with one alkyl group per silicon atom, a single addition product will be formed. If a sufficiently large excess of the fluorocompound is present, some of this excess will also add to at least some of the remaining alkyl groups bonded to the silicon atoms. However, complete additive exhaustion of all α-carbon atoms by the fluorinated reactant is unlikely because of steric hindrance.

The amount of the free radical generator is usually about 0.1-10% based on the weight of the organosilicon compound. Any one of the commercial free radical generators, and especially those recited in the Warrick patent, U.S. Pat. No. 2,958,707, can be used. While the temperature is not critical, it must be sufficiently high to allow free radical initiation of the reaction. The addition can be carried out neat or in the presence of a solvent. The usual solvent will be a hydrocarbon, such as benzene or petroleum ether, but it can be any other solvent which remains inert under the reaction conditions.

The adducts of the present invention are either liquid [of] *or* solid at room temperature. They are useful as (1) lubricants and sealants for the automotive and aerospace industries, (2) fire-resistant hydraulic fluids, and (3) siloxane elastomers having good oil and solvent resistance.

This invention is now illustrated by the following examples of certain preferred embodiments thereof, wherein all parts, proportions, and percentages are by weight unless otherwise indicated.

EXAMPLE 1

A stainless steel pressure vessel was charged with 50 g of octamethyltetracyclosiloxane and 2.0 g of di-t-butyl peroxide. The vessel was closed, cooled to −75° C., and evacuated twice. Hexafluoropropene, 250 g, was introduced, and the vessel was heated to 140° C. for 6 hours. During this time the pressure rose to 890 psi (6.1 MPa) and then slowly dropped to 750 psi (5.2 MPa). The reaction vessel was cooled to room temperature; the gases were vented; and the product was collected. The product was fractionally distilled and yielded the following cuts:

TABLE I

| Cut | Boiling Point | Weight g | % C | % H | % F |
|---|---|---|---|---|---|
| I[1] | — | 8 | — | — | — |

TABLE I-continued

| Cut | Boiling Point | Weight g | % C | % H | % F |
|---|---|---|---|---|---|
| II | 75° C./36 mm | 18.5 | 31.0 | 6.5 | 16.5 |
| III | 95-100° C./0.25 mm | 35 | 27.3 | 3.3 | 46.2 |
| IV | 110° C./0.25 mm | 18 | 26.8 | 2.6 | 53.6 |
| V[2] | — | 21 | 25.8 | 2.1 | 57.0 |

[1]Foreshot
[2]Heel
Cut III nmr: δ0.04-0.4 (m, 94), δ1.1-2.0 (m, 34), δ4.2-5.1 (d, 17)
Cut IV nmr: δ0.05-0.35 (m, 62) δ1.2-2.1 (m, 41), δ4.3-5.1 (d, 19)

The elemental analyses coupled with the nmr data indicate that Cut III is an adduct of three hexafluoropropene units with one octamethyltetracyclosiloxane (molar basis) while Cut IV is a 4:1 adduct.

EXAMPLE 2

Using the techniques described in Example I, the experiments summarized in Table II were performed. Unless specifically noted, the following quantities of the reactants and catalysts, were used: siloxane 100 g, fluorocompound 250 g, peroxide 2 g.

TABLE II

| Run | Reactants[1] | Reaction Temp. (°C.) | Weight Product (g) | Characterization Data |
|---|---|---|---|---|
| A | OMCTS<br>HFP<br>DTBP | 140 | 226 | % F: 1.6 |
| B | OMCTS<br>PMVE<br>DTBP | 140 | 310 | % F: 47.3 |
| [C | OMCTS<br>HFA<br>DTBP] | 140 | 185 | % F: 28.6 |
| D | Polydimethylsiloxane fluid (M.W. 460)<br>HFP<br>DTBP | 140 | 183 | % F: 36.2<br>M.W. 1440 |
| E | Polydimethylsiloxane fluid (M.W. 460)<br>HFP<br>DTBP | 140 | 169 | % F: 26.7 |
| F | Polydimethylsiloxane fluid (M.W. 460)<br>HFP<br>DTBP | 140 | 160 | % F: 40.5 |
| G | Polydimethylsiloxane fluid<br>HFP<br>DTBP | 140 | 177 | % F: 40.9 |
| H | Polydimethylsiloxane fluid (M.W. 460)<br>PMVE<br>DTBP | 140 | 313 | % F: 47.1 |
| I | Sample H<br>PMVE<br>DTBP | 140 | 220 | % F: 60.3<br>Tg: −69° C. |
| J | Sample E<br>HFP<br>DTBP | 140 | 150 | % F: 59.7 |
| [K | Polydimethylsiloxane fluid (M.W. 460)<br>HFA<br>DTBP | 140 | 200 | % F: 30.4 |
| L | HMCTS<br>HFA<br>DTBP | 140 | 160 | % F: 3.71% |
| M | HMCTS<br>HFA | 140 | 105[2] | % F: 44.7;<br>b.p. 45-50° C./0.15 mm |
| | DTBP | | 47[3] | % F: 47.6;<br>b.p. 80°C./mm] |
| N | 10% SE-30 silicone | 140 | — | % F: 54.3 |

TABLE II-continued

| Run | Reactants[1] | Reaction Temp. (°C.) | Weight Product (g) | Characterization Data |
|---|---|---|---|---|
| | rubber in benzene, 100 ml<br>HFP<br>DTBP: - 2.5 g | | | |
| O | 10% Se-30 silicone rubber in benzene; 100 ml<br>HFP<br>DTBP: - 2.5 g | 140 | — | % F: 60.4 |
| P | 10% SE-30 silicone rubber in benzene, 100 ml<br>HFP<br>DTBP | 140 | — | % F: 19.3 |
| Q | OMCTS<br>HFP<br>DTBP<br>BrTFE - 3 g | 140 | 189 | % F: 38.5<br>% Br: 1.3 |
| R | Polydimethylsiloxane fluid (M.W. 460)<br>HFP<br>BrTFE - 3 g | 140 | 189 | % F: 35.7<br>% Br: 0.9 |
| S | Polydimethylsilonane fluid (M.W. 669)<br>PMVE<br>DTBP | 140 | 319 | % F: 46.5<br>M.W. 1839 |
| T | Polydimethylsiloxane fluid (M.W. 450–20 g)<br>Perfluoropheptene-1 - 100 g<br>DTBP - 1 g | 140 | — | % F: 56.7 |
| U | Polydimethylsiloxane fluid (M.W. 169–20 g)<br>Perfluoropheptene-1 - 100 g<br>DTBP - 1.5 g | 140 | 47 | % F: 44.9 |

[1]ABBREVIATIONS
OMCTS octamethylcyclotetrasiloxane
HFP Hexafluoropropene
DTBP di-t-butyl peroxide
PMVE perfluoromethyl vinyl ether
[HFA hexafluoroacetone]
HMCTS hexamethylcyclotetrasiloxane
BrTFE bromoinfluoroethylene
[2]Distillation Cut 1
[3]Distillation Cut 2

What is claimed is:

1. A fluorine-containing organosilicon compound made by the addition to an organosilicon compound having at least one alkyl group attached to a silicon atom, at least one hydrogen atom being bonded to the carbon atom adjacent the silicon atom, of a fluorocompound selected from the class consisting of the following:

(A) fluoroolefins having one of the following formulas (1), (2), and (3):

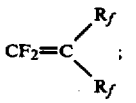

(1)

-continued

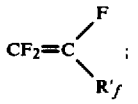

(2)

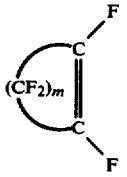

(3)

[(B) ketones having the following formula (4):]

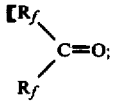

(4)

and (C) ethers having the following formula [(5)] (4)

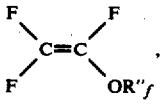

[(5)] (4)

where

Each $R_f$ independently is a $C_1$–$C_8$ saturated perfluoroalkyl;

$R'_f$ is Br or $R_f$;

$R''_f$ is $R_f$ or a radical obtained by removing one fluorine atom from a perfluoroalkyl ether; and m in formula (3) is an integer of 2 to 12.

2. A compound of claim 1, which is an adduct of a fluorocompound with a linear or cyclic siloxane.

3. A compound of claim 2, wherein the siloxane has the following formula

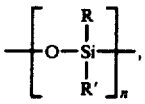

wherein each of R and R′ is alkyl; if the siloxane is cyclic, n is 3–6; and if the siloxane is linear, n is 2–10,000 and is represented by the formula

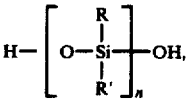

4. A compound of claim 1 which is an adduct of an organosilicon compound with a fluorocompound selected from the group consisting of hexafluoropropene, perfluoromethyl vinyl ether, [hexafluoroacetone,] and bromotrifluoroethylene.

* * * * *